United States Patent

Haas et al.

[11] 4,112,099
[45] Sep. 5, 1978

[54] CYCLO ALIPHATIC-PHENYLENE-CARBONYL-PYRIDINES

[75] Inventors: Georges Haas; Alberto Rossi, both of Oberwil, Switzerland

[73] Assignee: Ciba-Geigy Corporation, Ardsley, N.Y.

[21] Appl. No.: 680,947

[22] Filed: Apr. 28, 1976

Related U.S. Application Data

[62] Division of Ser. No. 443,289, Feb. 19, 1974, Pat. No. 3,980,657.

[30] Foreign Application Priority Data

Feb. 19, 1973 [CH] Switzerland ............... 2381/73
Oct. 23, 1973 [CH] Switzerland ............... 14936/73

[51] Int. Cl.$^2$ .............. A61K 31/44; C07D 213/50
[52] U.S. Cl. .............. 424/263; 260/294.8 R; 260/295 S; 260/295 F; 260/295 T; 260/296 M; 260/296 B; 260/296 T; 260/297 R; 260/297 B; 260/297 T
[58] Field of Search ............ 260/297 R, 297 B, 29 T, 260/294.8 B, 294.8 D, 294.8 R, 295 F, 295 T, 295 R, 297 R, 297 B, 297 T, 295 S; 424/263

[56] References Cited

U.S. PATENT DOCUMENTS 3,262,937 7/1966 Pesson .................. 260/293.75
3,795,677 3/1974 Carr et al. ............. 260/293.62

OTHER PUBLICATIONS

Burger, Medicinal Chemistry, Second Edition, Interscience Pub., pp. 497, 1960.

*Primary Examiner*—Alan L. Rotman
*Attorney, Agent, or Firm*—John J. Maitner

[57] ABSTRACT

New pyridine compounds of the general formula I

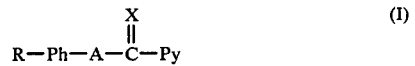

wherein R denotes an optionally substituted cycloaliphatic hydrocarbon radical, Ph denotes an ortho-phenylene radical or especially a para-phenylene radical, A denotes a lower alkylene radical or a direct bond, X denotes an optionally functionally modified oxo group and Py denotes a pyridine radical, are useful as fibrinolytics, thrombolytics, antiphlogistics and as mild analgesics.

9 Claims, No Drawings

CYCLOALIPHATIC-PHENYLENE-CARBONYL-PYRIDINES

This is a division, of application Ser. No. 443,289, filed Feb. 19, 1974 (now U.S. Pat. No. 3,989,547).

The invention relates to new pyridine compounds of the general formula I

wherein R denotes an optionally substituted cycloaliphatic hydrocarbon radical, Ph denotes an ortho-phenylene radical or especially a para-phenylene radical, A denotes a lower alkylene radical or a direct bond, X denotes an optionally functionally modified oxo group and Py denotes a pyridine radical, in free form or in the form of a salt.

The cycloaliphatic hydrocarbon radical R can monocyclic or oligocyclic, in particular bicyclic, tricyclic or tetracyclic. Monocyclic radicals R are, for example, cycloalkyl radicals or cycloalkenyl radicals, especially 1-cycloalkenyl radicals, above all those with 4 to 12, preferably 5 to 10, ring members, such as cyclobutyl, cycloundecyl, cyclododecyl, 3- or 4-cyclopentenyl, 3- or 4-cyclohexenyl, 3-, 4- or 5-cycloheptenyl, 3-, 4- or 5-cyclooctenyl or preferably cyclopentyl, cyclohexyl, cycloheptyl, cyclooctyl, cyclononyl or cyclodecyl or especially 1-cyclobutenyl, 1-cycloundecenyl or 1-cyclododecenyl or preferably 1-cyclopentenyl, 1-cyclohexenyl, 1-cycloheptenyl, 1-cyclooctenyl, 1-cyclononenyl or 1-cyclodecenyl. Bicyclic radicals R preferably contain 5 to 7 ring members which have 1 to 4, preferably 2 or 3, C atoms in common. As examples, there may be mentioned 2- and 3-bicyclo[4,4,0]decyl and -dec-2-enyl, 2-bicyclo[2,2,2]octyl and -oct-2-enyl, 2-bornyl, 2-norbornyl, 2-bornenyl and 2-norbornenyl. As tricyclic and tetracyclic radicals R there should in particular be mentioned homoadamantyl, for example 1-homoadamantyl, octahydro-1,2-4-methenopentalenyl, twistanyl, bullvalenyl and above all 1- and 2-adamantyl. Possible substituents of the cycloaliphatic hydrocarbon radical are in particular lower alkyl, alkoxy or alkenyl radicals or acyloxy, hydroxyl or oxo groups, primary amino groups or N-mono- or N,N-di-lower alkylamino groups.

The phenylene radical Ph can be unsubstituted or mono-substituted, disubstituted or polysubstituted. Examples of possible substituents are lower alkyl or alkoxy radicals, halogen atoms or acylamino groups, especially those mentioned below, or amino, nitro, trifluoromethyl or hydroxyl groups.

The lower alkylene radical A is in particular a 1,1-, 1,2- or 1,3-alkylene radical with up to 8, above all with up to 4, carbon atoms, and can be straight-chain or branched. As examples there may be mentioned: 1,3-, 1,2- or 2,3-butylene, 1,3-isobutylene, 1,1- or 2,2-butylidene or 1,1-isobutylidene or above all 1,3- or 1,2-propylene or especially propylidene, isopropylidene, ethylidene, ethylene or methylene.

A functionally modified oxo group X is in particular a group which can be converted easily, for example hydrolytically, into the oxo group, such as an imino group, for example the free imino group or an imino group substituted by a hydrocarbon radical, above all an aromatic hydrocarbon radical, such as a phenyl radical optionally substituted as indicated for radicals Ph, or a hydroxyimino group which is optionally etherified, for example with a lower alkanol, or esterified, for example with an organic acid, such as a carboxylic acid or an organic sulphonic acid, or a ketalised or thioketalised oxo group, in which case a lower alkanol, for example ethanol, methanol or butanol, or a lower alkanediol, for example ethylene glycol or a propylene glycol, should above all be mentioned as the ketal-forming alcohol, and a lower alkylmercaptan, for example butylmercaptan, or a lower alkyldimercaptan, for example 1,2-dimercaptoethane or 1,3-dimercaptopropane, should above all be mentioned as the thioketal-forming mercaptan.

The pyridyl radical Py is bonded in the 2-, 3- or 4-position and can be monosubstituted, disubstituted or polysubstituted at the carbon atoms and/or be quaternised by lower alkyl or alkenyl radicals and/or be N-oxidised. Possible C-substituents are above all alkyl radicals, such as lower alkyl radicals, especially those mentioned below, or alkoxy radicals, such as lower alkoxy radicals, especially those mentioned below.

In the preceding and following text, a lower radical is in particular understood as a radical with up to 7 C atoms, above all with up to 4 C atoms.

A lower alkyl radical is, for example, the methyl, ethyl, propyl or isopropyl radical or a straight or branched butyl, pentyl or hexyl radical bonded in any desired position.

A lower alkenyl radical is, for example, the allyl or methallyl radical.

A lower alkoxy radical is, in particular, a lower alkoxy radical which contains one of the abovementioned lower alkyl radicals, above all a straight or branched butoxy, pentyloxy or hexyloxy radical bonded in any desired position or, preferably, the methoxy, ethoxy, propoxy or isopropoxy radical.

A N-mono- or N,N-di-lower alkylamino radical is in particular an amino group substituted by one or two of the abovementioned lower alkyl radicals, above all a straight or branched N-mono- or N,N-di-butyl-, -pentyl- or -hexyl-amino radical bonded in any desired position or preferably the N-mono- or N,N-di-isopropyl-, -propyl-, -ethyl- or -methyl-amino radical.

An acyl radical is in particular the radical of a carboxylic acid, such as of a lower alkanecarboxylic acid, for example of formic acid, acetic acid or propionic acid, or of one of the isomeric butyric, valeric, caproic or oenanthic acids, or of an aromatic carboxylic acid, for example of a benzoic acid which is optionally substituted as indicated for the radical Ph, or the radical of an organic sulphonic acid, such as of a lower aliphatic or of an aromatic sulphonic acid, for example of methanesulphonic acid, ethanesulphonic acid, ethenesulphonic acid, benzenesulphonic acid, p-bromobenzenesulphonic acid or p-toluenesulphonic acid.

An acyloxy radical is in particular a lower alkanoyloxy radical or a benzoxy radical which is optionally substituted as indicated for the radicals Ph, for example the formyloxy, acetoxy, propionyloxy, butyryloxy or benzoyloxy radical.

An acylamino radical is in particular a lower alkanoylamino radical or a benzoylamino radical which is optionally substituted as indicated for the radicals Ph, for example the formylamino, acetylamino, propionylamino, butyrylamino or benzoylamino radical.

A halogen atom is above all the fluorine, chlorine or bromine atom.

The new compounds possess valuable pharmacological properties, above all a fibrinolytic action as well as an antinociceptive (analgesic) and anti-inflammatory action.

Thus, when 3 to 30 mg/kg are administered orally to rats, they cause a distinct reduction of the euglobulin clot lysis time (Pharamacology 4,242, 1970) and a normalisation of the euglobulin clot lysis time of the oedema of the paw produced by kaolin. Furthermore they produce, in vitro, at a concentration of 300 to 600 μg/ml, an activation of the plasma clot lysis time of human blood plasma.

Furthermore, on oral administration of 30 to 300 mg/kg to mice they show, in the phenyl-p-benzoquinone writhing test, a distinct antinociceptive (analgesic) action, whilst in the kaolin oedema test on the paws of rats they show a distinct anti-inflammatory action on oral administration in a dose of 10 to 100 mg/kg.

The new compounds are therefore useful as fibrinolytics, thrombolytics, antiphlogistics and mild analgesics. However, they are also valuable intermediate products for the manufacture of other useful materials, especially of pharmacologically active compounds.

Special mention is required of the group Ia of those compounds of the formula I wherein R denotes a monocyclic, bicyclic, tricyclic or tetracylic aliphatic hydrocarbon radical which is optionally substituted by lower alkyl, alkenyl, alkoxy or acyloxy radicals or hydroxyl or oxo groups or optionally N-mono- or N,N-di-lower alkylated amino groups, Ph denotes a p-phenylene radical which is optionally substituted by amino, acylamino, nitro, trifluoromethyl or hydroxyl groups or especially lower alkyl or alkoxy groups or halogen atoms, A denotes a 1,1-, 1,2- or 1,3-alkylene radical with up to 7 C atoms or a direct bond, X denotes the imino or hydroxyimino group or an optionally ketalised or thioketalised oxo group and Py denotes a pyridyl radical which is optionally substituted by lower alkyl or alkoxy radicals, quaternised by a lower alkyl or alkenyl radical and/or N-oxidised.

A group Ib to be singled out are those compounds of the formula I wherein R denotes a cycloalkyl or cycloalkenyl radical with 4 to 12 ring members which is optionally substituted by lower alkyl, alkenyl, alkoxy or acyloxy radicals or hydroxyl or oxo groups or an optionally N-mono- or N,N-di-lower alkylated amino group, or denotes 2- or 3-bicyclo[4,4,0]decyl or -dec-2-enyl, 2-bicyclo[2,2,2]octyl or -oct-2-enyl, 2bornyl, 2-norbornyl, 2-norbornenyl, 2-bornenyl, 1-homoadamantyl, octahydro-1,2,4-methenopentalenyl, twistanyl, bullvalenyl or 1- or 2-adamantyl, optionally substituted by lower alkyl, alkoxy or alkenyl groups or hydroxyl or oxo groups, Ph denotes a p-phenylene radical which is optionally substituted by amino, lower acylamino, nitro, hydroxyl, lower alkyl or lower alkoxy groups and/or halogen atoms, A denotes 1,3-, 1,2- or 2,3-butylene, 1,3-isobutylene, 1,1-, or 2,2-butylidene or 1,1-isobutylidene or above all 1,3- or 1,2-propylene or especially propylidene, isopropylidene, ethylidene, ethylene or methylene or a direct bond, X denotes the imino or hydroxyimino group or an optionally ketalised or thioketalised oxo group and Py denotes a pyridyl radical which is optionally substituted by lower alkyl or alkoxy radicals, quaternised by a lower alkyl or alkenyl radical and/or N-oxidized.

A group Ic to be singled out particularly are those compounds of the formula I wherein R denotes a cycloalkenyl or cycloalkyl radical with 5 to 10 ring members which is optionally substituted by lower alkyl, alkenyl or alkoxy radicals or hydroxyl or oxo groups, or denotes optionally lower alkylated or lower alkoxylated 2- or 3-bicyclo[4,4,0]-decyl or -dec-2-enyl, 2-bicyclo[2,2,2]octyl or -oct-2-enyl, 2-bornyl, 2-norbornyl, 2-bornenyl, 2-norbornenyl, 1-homoadamantyl, octahydro-1,2,4-methenopentalenyl or 1- or 2-adamantyl, Ph denotes p-phenylene optionally substituted by nitro or trifluoromethyl groups or above all lower alkyl or alkoxy groups or chlorine, fluorine or bromine atoms, A denotes 1,3- or 1,2-propylene or especially propylidene, isopropylidene, ethylene or above all methylene, ethylidene or a direct bond, X denotes the imino or hydroxyimino group or an oxo group which is optionally ketalised with a lower alkanol or alkanediol or thioketalised with a lower alkylmercaptan or dimercaptoalkane, and Py denotes a pyridyl radical which is optionally substituted by lower alkyl or alkoxy radicals, quaternised by a lower alkyl or alkenyl radical and/or N-oxidised.

A group Id to be singled out above all are those compounds of the formula I wherein R denotes a cycloalkyl or cycloalkenyl radical with 5–8 ring members which is optionally substituted by lower alkyl, alkenyl or alkoxy radicals, or denotes optionally lower alkylated 2- or 3-bicyclo[4,4,0]-decyl or -dec-2-enyl, 2-bicyclo[2,2,2]octyl or -oct-2-enyl, 2-bornyl, 2-norbornyl, 2-bornenyl, 2-norbornenyl, 1-homoadamantyl or 1- or 2-adamantyl, Ph denotes p-phenylene which is optionally substituted by nitro or trifluoromethyl groups or above all lower alkyl or alkoxy groups or chlorine, fluorine or bromine atoms, A denotes 1,3- or 1,2-propylene, propylidene, isopropylidene, ethylene, methylene, ethylidene or a direct bond, X denotes the imino or hydroxyimino group or an oxo group which is optionally ketalised with a lower alkanol or alkanediol or thioketalised with a lower alkylmercaptan or dimercaptoalkane and Py denotes a pyridyl radical which is optionally substituted by lower alkyl or alkoxy radicals, quaternised by a lower alkyl or alkenyl radical and/or N-oxidised.

However, a group Ie which should be singled out very particularly are those compounds of the formula I wherein R denotes 3- or 4-cyclopentenyl, 3- or 4-cyclohexenyl, 3-, 4- or 5-cycloheptenyl or 3-, 4- or 5-cyclooctenyl which are optionally substituted by a lower alkyl or alkoxy group, or denotes unsubstituted 2- or 3-bicyclo[4,4,0]decyl or -dec-2-enyl, 2-bicyclo[2,2,2]octyl, 2-bornyl, 2-norbornyl or above all denotes cyclopentyl, cyclohexyl, cycloheptyl, cyclooctyl, 1-cyclopentenyl, 1-cyclohexenyl, 1-cycloheptenyl or 1-cyclooctenyl which are optionally substituted by a lower alkyl or alkoxy group, or denotes unsubstituted 1- or 2-adamantyl, Ph denotes p-phenylene which is optionally substituted by nitro or trifluoromethyl groups or above all lower alkyl or alkoxy groups or chlorine, fluorine or bromine atoms, A denotes 1,3- or 1,2-propylene or especially propylidene, isopropylidene, ethylene or above all methylene, ethylidene or a direct bond, X denotes the imino or hydroxyimino group or an oxo group which is optionally ketalised with a lower alkanol or alkanediol or thioketalised with a lower alkylmercaptan or dimercaptoalkane and Py denotes a pyridyl radical which is optionally substituted by lower alkyl or alkoxy radicals, quaternised by a lower alkyl or alkenyl radical and/or N-oxidised.

A valuable group is above all the group If of those compounds of the formula I wherein R denotes optionally methylated or methoxylated 3- or 4-cyclopentenyl, 3- or 4-cyclohexenyl, 3-, 4- or 5-cycloheptenyl, 3-, 4- or 5-cyclooctenyl or above all cyclopentyl, cycloheptyl, cyclooctyl, 1-cyclopentenyl, 1-cyclohexenyl, 1-cycloheptenyl or 1-cyclooctenyl or unsubstituted 1- or 2-adamantyl, Ph denotes p-phenylene optionally substituted by methyl, ethyl, methoxy, ethoxy, chlorine or bromine, A denotes propylidene, isopropylidene, ethylene or above all methylene, ethylidene or a direct bond, X denotes the imino or hydroxyimino group or above all the oxo group and Py denotes a pyridyl radical which is optionally substituted by methyl or methoxy, quaternised by methyl or ethyl and/or N-oxidised.

A particularly valuable group is the group Ig of those compounds of the formula I wherein R denotes optionally methylated or methoxylated cyclopentyl, cyclohexyl, chycloheptyl, cyclooctyl, 1-cyclopentenyl, 1-cyclohexenyl, 1-cycloheptenyl or 1-cyclooctenyl or unsubstituted 1- or 2-adamantyl, Ph denotes p-phenylene optionally substituted by methyl, methoxy or chlorine, A denotes propylidene, isopropylidene, ethylene or above all methylene, ethylidene or a direct bond, X denotes the imino or hydroxyimino group or above all the oxo group and Py denotes a pyridyl radical which is optionally substituted by methyl or methoxy, quaternised by methyl or ethyl and/or N-oxidised.

A very particularly valuable group is the group Ih of those compounds of the formula I wherein R denotes cyclopentyl, 1-cyclopentenyl, cyclooctyl, 1-cyclooctenyl or above all cyclohexyl, 1-cyclohexenyl, cycloheptyl, 1-cycloheptenyl or 2- or 1-adamantyl, Ph denotes p-phenylene optionally substituted by methyl, methoxy or chlorine, especially in the o-position to R, X denotes the imino, hydroxyimino or oxo group, A denotes propylidene, isopropylidene, methylene or above all ethylidene or a direct bond and Ph denotes an optionally C-methylated or N-oxidised pyridyl radical.

However, a group which deserves special mention is the group Ii of those compounds of the formula I wherein R denotes cyclohexyl, 1-cyclohexenyl, 1-cycloheptenyl or 1-adamantyl, Ph denotes p-phenylene optionally chlorinated in the o-position to R, X denotes the oxo group, A denotes ethylidene or a direct bond and Py denotes an optionally C-methylated pyridyl radical, and specifically 2-[(3-chloro-4-cyclohexyl-phenyl)-oxomethyl]-pyridine, 2-[2-(3-chloro-4-cyclohexyl-phenyl)-1-oxo-propyl]-pyridine, 4-{2-[p-(1-cyclohexenyl)-phenyl]-1-oxo-propyl}-pyridine, 2-{2-[p-(1-cyclohexenyl)-phenyl]-1-oxo-propyl}-6-methylpyridine, 2-{[p-(1-cyclohexenyl)-phenyl]-oxomethyl}-pyridine, 2-[2-(p-cyclohexylphenyl)-1-oxo-propyl]-pyridine, 2-[(p-cyclohexylphenyl)-oxomethyl]-pyridine, 3-[(p-cyclohexylphenyl)-oxomethyl]-pyridine, 2-{2-[p-(1-cyclohexenyl)-phenyl]-1-hydroxyimino-propyl}-pyridine and 2-{2-[p-(1-cyclohexenyl)-phenyl]-1-oxo-propyl}-pyridine.

The new compounds are obtained according to methods which are in themselves known.

Thus the new compounds, especially those compounds of the formula I wherein R is optionally substituted by lower alkyl, alkenyl, alkoxy or N,N-dialkylamino groups and Ph is optionally substituted by alkyl, alkoxy or trifluoromethyl groups or chlorine or fluorine, can be manufactured, for example, by reacting a compound of the formula II

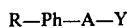

R—Ph—A—Y (II)

with a compound of the formula III

Z—Py (III)

wherein, R, Ph, A and Py have the indicated meanings, Y represents an optionally functionally modified carboxyl group and Z represents a magnesium atom, this atom being bonded by means of the free valency to a second radical Py- or R-Ph-A- or preferably to chlorine, iodine or bromine, or a sodium, potassium or lithium atom.

A functionally modified carboxyl group is the nitrile group, or a functionally modified carboxyl group containing an oxo group, such as an anhydridised or esterified carboxyl group. An anhydridised carboxyl group is in particular a carboxyl group anhydridised with a strong acid, above all with a strong inorganic acid, such as a hydrogen halide acid, for example with hydrobromic acid or preferbly with hydrochloric acid. An esterified carboxyl group is in particular a carboxyl group esterified with an aliphatic or araliphatic alcohol, such as a lower alkanol, for example a lower alkanol corresponding to one of the lower alkyl radicals mentioned or singled out, preferably with methanol, ethanol, propanol, isopropanol or one of the isomeric butanols, or a phenylalkanol optionally substituted as indicated for Ph, for example with benzyl alcohol or phenylethanol.

A metal atom Z is in particular to be understood as a sodium, potassium or above all lithium atom, a group of the formula -Mg-Hal, wherein Hal represents chlorine or above all iodine or bromine.

The reaction can be carried out in a manner which is in itself known, for example in an inert solvent, preferably an aprotic polar solvent, such as a lower aliphatic ether, for example in dibutyl ether or above all diethyl ether or diisopropyl ether, or a cyclic ether, for example in dioxane or above all tetrahydrofurane, but also, for example in the case of the reaction with cadmium compounds, in a hydrocarbon, preferably an aromatic hydrocarbon, such as in benzene, or, for example in the case of the reaction of lithium compounds, in a mixture of an ether and a preferably aliphatic hydrocarbon, above all an alkane, such as in tetrahydrofurane/hexane, and preferably at lowered, normal or moderately raised temperature.

Thus it is possible, in a preferred embodiment of the above process, to react a compound of the formula II, wherein R and Ph have the indicated meanings, A represents a direct bond and Y denotes the free carboxyl group or the nitrile group, in an ether, such as diethyl ether or tetrahydrofurane, with a compound of the formula III, wherein Py has the indicated meaning and Z represents a lithium atom, to give a corresponding compound of the formula I, wherein X denotes the oxo group or the imino group, the reaction of acids of the formula II preferably being carried out between −100° C and room temperature, above all at −80° C to 0° C, and the reaction of nitriles of the formula II at temperatures between −30° C or, above all, 0° C, and the boiling point of the solvent used.

The new compounds can also be manufactured by reacting a compound of the formula IV

Py — Y₂ (IV)

with a compound of the formula V $$R - Ph - H \quad (V)$$

wherein Py, R and Ph have the indicated meanings and $Y_2$ represents an acid halide grouping, for example an acid chloride grouping.

The reaction is carried out in the usual manner, preferably in the presence of a catalyst, such as a Lewis acid, such as a halide of aluminium, for example in the presence of aluminium chloride or aluminium bromide in an inert solvent, such as an ether, for example in diethyl ether, tetrahydrofurane or dioxane, or in a chloroalkane, for example in carbon tetrachloride, in an alkane, for example in a high-boiling benzine fraction, or in carbon disulphide, at normal or optionally moderately raised temperature.

In resulting compounds, substituents can be introduced, modified and split off within the scope of the definition of the end products.

Thus, for example, it is possible, in resulting compounds wherein R denotes an unsaturated cycloaliphatic hydrocarbon radical, to convert this radical into a saturated radical R by reaction of the olefinic double bond or bonds. The reduction is carried out in the customary manner, preferably by treatment with hydrogen in the presence of hydrogenation catalysts, such as nickel catalysts, platinum catalysts or palladium catalysts, for example with Raney nickel, platinum oxide or palladium on charcoal, suitably in an inert solvent, such as a lower alkanol, for example in ethanol or methanol, or a lower aliphatic carboxylic acid, for example acetic acid, advantageously at elevated pressure and/or elevated temperature, but also by means of nascent hydrogen.

On the other hand it is possible, in resulting compounds in which the radical R carries a radical which can be eliminated, such as a hydroxyl group, acyloxy group or a — preferably lower-alkylated — amino group, to introduce a double bond, which may be an additional double bond, by elimination of the radical which can be eliminated and of a hydrogen atom, in the α-position thereto, in the radical R. The elimination is carried out in the usual manner, for example thermally and advantageously in the presence of a suitable catalyst, such as a proton acid, such as a strong inorganic acid, for example hydrochloric acid or hydrobromic acid or sulphuric acid or phosphoric acid, or an acid salt thereof, or an acid ion exchanger or aluminium oxide or silicon oxide, suitably in a partially hydrated form.

It is furthermore possible, in resulting compounds in which the radical R carries an acyloxy group, to hydrolyse this group to the hydroxyl group in the usual manner, for example in the presence of acid or basic catalysts, such as those mentioned.

Conversely, however, it is also possible to acylate free hydroxyl groups to acyloxy groups in the usual manner by acylation, for example by reaction with an acid anhydride or acid halide, if desired in the presence of acid-binding agents.

In resulting compounds, the radical Ph and/or the radical Py can be halogenated in the usual manner, for example by reaction with chlorine or bromine, preferably in the presence of a catalyst, for example of iron-(III) chloride, or by reaction with N-chlorosuccinimide. On the other hand, the halogen present can be replaced by hydrogen in the usual manner, for example by means of hydrogen in the presence of a catalyst, such as palladium, platinum oxide or Raney nickel, or by the action of a trialkyl-tin hydride, for example triethyl-tin hydride. It is also possible to introduce trifluoromethyl groups, for example by reaction of trifluoromethyl iodide in the presence of metals, for example copper powder. Furthermore, alkyl groups can be introduced, for example by reaction with an alkyl halide, advantageously in the presence of a catalyst, such as a metal halide, for example aluminium chloride or aluminium bromide.

In resulting compounds in which the radical Ph is substituted by nitro, a nitro group or, if appropriate, more than one nitro group, can be reduced in the usual manner to the amino group, for example by the action of nascent hydrogen generated in the usual manner, for example by means of iron and hydrochloric acid.

In resulting compounds in which the radical Ph is substituted by amino, the amino group or groups can be acylated in the usual manner, for example by reaction with an acylating agent, such as an acid anhydride or an acid halide. Conversely, it is also possible to deacylate acylamino groups which are present, in the usual manner, for example hydrolytically, if desired in the presence of acid or basic catalysts.

In resulting compounds in which the radical Ph is substituted by amino, the amino group or groups can be replaced by halogen, for example bromine or chlorine, in the usual manner, for example by customary diazotisation, for example by means of nitrous acid, followed by reaction with an at least equimolecular amount of a corresponding metal halide, for example copper-(I) halide, or can be replaced by the hydroxyl group or the radical of an alcohol, for example lower alkoxy, by subsequent reaction with water or an alcohol, for example a lower alkanol.

In resulting compounds in which the radical Ph is hydroxylated, the hydroxyl group or groups can furthermore be etherified with an alcohol in the usual manner, for example by reaction therewith, preferably in the presence of a strong base, such as potassium hydroxide or sodium hydroxide, or especially by reaction with a corresponding halide, for example chloride or bromide, in the presence of an acid-binding agent, preferably in the presence of potassium carbonate in amyl alcohol.

Furthermore, resulting compounds wherein the radical A denotes an alkylidene radical which carries at least one hydrogen atom in the α-position to CX, for example the methylene, ethylidene, 1,1-propylene or 1,1-butylene radical, can be α-alkylated in the usual manner.

For example, the compound to be alkylated can be converted into an α-metal salt, for example by reaction with a strong base, such as an alkali metal amide, alkali metal hydride or alkali metal hydrocarbon compound, for example with sodium amide, sodium hydride, phenyl-lithium or butyl-lithium or diisopropyl-lithium amide, and this salt can then be reacted, preferably without isolation, with a reactive ester of a corresponding alkanol. Reactive esters are, in particular, those with strong inorganic or organic acids, preferably with hydrogen halide acids, such as hydrochloric acid, hydrobromic acid or hydriodic acid, sulphuric acid or arylsulphonic acid, such as benzenesulphonic acid, p-bromo-benzenesulphonic acid or p-toluenesulphonic acid.

In resulting compounds, groups -X can also be converted into one another.

Thus, for example, functionally modified oxo groups can be converted into the free oxo group in the usual manner, for example hydrolytically.

The hydrolysis to the free oxo group can be carried out in the customary manner, for example in the presence of a strong base, such as an alkaline earth metal or alkali metal hydroxide or carbonate or an organic base, for example a tertiary nitrogen base, or especially in the presence of an acid, for example sulphuric acid, hydrochloric acid or hydrobromic acid, or a strong organic acid, for example a carboxylic acid, such as acetic acid, or an organic sulphonic acid, such as p-toluenesulphonic acid, p-bromobenzenesulphonic acid, methanesulphonic acid or benzenesulphonic acid. Carrying out the hydrolysis under acid conditions is to be recommended particularly for the hydrolysis of ketalised and thioketalised oxo groups.

However, the hydroxyimino group can also be converted into the oxo group by reaction with a metal alcoholate, for example with aluminium isopropylate, and subsequent rearrangement.

In the hydrolysis of the thioxo group and of thioketalised oxo groups, it is preferable to operate in the presence of heavy metal salts or oxides which form sparingly soluble mercaptides with mercaptans, or particularly in the presence of an oxidising agent. Examples of suitable oxidising agents are hydrogen peroxide, potassium permanganate or per-acids, for example aliphatic or aromatic per-acids, such as peracetic acid or perbenzoic acid. It is preferable to operate in a polar, aqueous solvent, for example acetic acid-water, and temperatures of about 20°–120° C are appropriate. In the hydrolysis of cyclic ketals, for example dithiolanes, oxathiolanes, oxathianes and dithianes, the use of a salt of a N-chlorinated sulphonamide, for example the sodium salt of N-chloro-N-p-toluenesulphonamide, is particularly advantageous.

Conversely, in resulting compounds in which X represents the oxo group, it is possible to modify the latter functionally in a customary manner, for example by reaction with an acetal or ketal, for example a 2,2-dialkoxypropane, for example with 2,2-dimethoxypropane, an optionally substituted 1,3-dioxolane or 1,3-dioxane or an orthocarboxylic acid lower alkyl ester, for example an orthoformic or orthoacetic acid lower alkyl ester, such as orthoformic acid ethyl or methyl ester, or by reaction with an alkane(di)ol or an alkyl(ene-di)mercaptan, preferably in the presence of a catalyst, for example a strong acid or especially a base, such as one of those mentioned, and with the water of reaction being bound or removed, for example by means of a dehydrating agent, for example dicyclohexylcarbodiimide or 1-ethoxycarbonyl-2-ethoxy-1,2-dihydroquinoline, or by means of azeotropic distillation, for example by adding benzene or toluene.

In resulting compounds in which X is thioxo, it is possible to convert X into the oxo group in the customary manner, especially by methods of hydrolysis which are in themselves known, for example by treating the resulting thioxo compound with an alkaline agent, such as an alkali metal hydroxide, in the presence of an oxidising agent, such as hydrogen peroxide.

In resulting compounds in which X is oxo, it is possible to convert X into the thioxo group in the customary manner, especially by treating the resulting oxo compound with suitable sulphides, such as phosphorus pentasulphide, aluminium sulphide, silicon disulphide or boron sulphide.

Resulting compounds in which X represents the oxo group can also be converted into the corresponding imines or oximes in the customary manner, for example by reaction with a primary amine or, above all with ammonia or above all with hydroxylamine, optionally in the presence of a catalyst such as a strong acid, for example one of those mentioned, and optionally in the presence of dehydrating agents, such as carbodiimides or 2-ethoxy-ethoxycarbonyl-1,2-dihydroquinoline.

Resulting compounds in which the radical Py is not substituted on the nitrogen atom can be N-oxidised in the customary manner and/or quaternised, for example by reaction with a strong alk(en)ylating agent, such as a reactive ester of an alkanol or alkenol.

The quaternisation is carried out in the customary manner, it being advantageous to use as starting material an iodide or bromide as the reactive ester.

The oxidation is carried out in the customary manner, for example with N-oxidising agents, such as hydrogen peroxide, ozone, inorganic per-acids, for example persulphuric acids such as Caro's acid, or especially organic peroxy compounds, above all organic per-acids, such as peracetic acid, pertrifluoroacetic acid, perbenzoic acid or monoperphthalic acid, which can also be substituted, for example by halogen atoms, such as chlorine atoms, for example chloromonoperphthalic acid or m-chloroperbenzoic acid, or tertiary hydroperoxide compounds, such as tert.-butyl peroxide or cumene peroxide, if necessary in the presence of catalysts such as vanadium, titanium or molybdenum compounds. In resulting compounds in which the radical Py is N-oxidised, Py can be converted into the corresponding pyridyl group which is not oxidised on the N-atom in a manner which is in itself known, for example by reduction. The reduction can be carried out with hydrogen activated catalytically, for example with a transition metal catalyst, such as a nickel, palladium or platinum catalyst, preferably in a solvent, such as a lower alkanol, for example methanol or ethanol. It is, however, also possible to use chemical reducing agents, for example complex hydrides of boron or of aluminium, such as lithium aluminium hydride, preferably in an ether-like liquid, such as a di-lower alkyl ether, for example diethyl ether, and also sulphur or derivatives thereof at a lower stage of oxidation, for example sodium dithionite or sulphur dioxide.

Depending on the process conditions and starting substances, final substances, which may form salts, are obtained in the free form or in the form of their salts, which can be converted into one another or into other salts in the customary manner. Acidic end products, that is to say those in which a phenolic hydroxyl group is present, are thus obtained in the free form or in the form of their salts with bases. The resulting free acidic compounds can be converted in the customary manner, for example by reaction with corresponding basic agents, into the salts of bases, above all into therapeutically usable salts of bases, for example salts of organic amines or metal salts. Possible metal salts are above all alkali metal salts or alkaline earth metal salts, such as sodium, potassium, magnesium or calcium salts. Free acids can be liberated from the salts in the customary manner, for example by reaction with acidic agents. End products with a basic character can also be obtained in the free form or in the form of their salts. The salts of the basic end products can be converted into the free bases in a manner which is in itself known, for example with alkalis or ion exchangers. Salts can be obtained from the latter by reaction with organic or inorganic acids, especially those which are suitable for the formation of therapeutically usable salts. The following examples of such acids may be mentioned: hydrogen halide acids, sulphuric acids, phosphoric acids, nitric acid, perchloric acid, aliphatic, alicyclic, aromatic or heterocyclic carboxylic or sulphonic acids, such as formic acid, acetic acid, propionic acid, succinic acid, glycollic acid, lactic acid, malic acid, tartaric acid, citric acid, ascorbic acid, maleic acid, hydroxymaleic acid or pyruvic acid; phenylacetic acid, benzoic acid, p-aminobenzoic acid, anthranilic acid, p-hydroxybenzoic acid, salicylic acid or p-aminosalicylic acid, embonic acid, methanesulphonic acid, ethanesulphonic acid, hydroxyethanesulphonic acid or ethylenesulphonic acid; halogenobenzenesulphonic acids, toluenesulphonic acid or naphthalenesulphonic acids or sulphanilic acid; methionine or tryptophane, lysine or arginine.

The salts can also be used for the purification of the new compounds, for example by converting the free compounds into their salts, isolating the latter and once more converting them into the free compounds. Owing to the close relationships between the new compounds in the free form and in the form of their salts, in the preceding and following text the free compounds are also to be understood, where appropriate, as the corresponding salts, with regard to general sense and intended use.

The new compounds can be in the form of optical antipodes, racemates or mixtures of isomers (for example mixtures of racemates), depending on the choice of starting substances and procedures and on the number of asymmetric carbon atoms.

The resulting mixtures of isomers (mixtures of racemates) can be separated, by virtue of the physico-chemical differences of the constituents, into the two stereoisomeric (diastereomeric) pure isomers (for example racemates) in a known manner, for example by chromatography and/or fractional crystallisation.

Resulting racemates can be split up into the diastereomers by known methods, for example by recrystallisation from an optically active solvent, with the aid of micro-organisms, or by reacting a free carboxylic acid with an optically active base which forms salts with the racemic compound and separating the salts obtained in this manner, for example by virtue of their different solubilities, and the antipodes can be liberated from the diastereomers by the action of suitable agents. A particularly customary optically active base is, for example, the D- and L-form of cinchonine. It is advantageous to isolate the more active of the two antipodes.

Resulting racemates of basic compounds can also be split up into the diastereomers by reaction with an optically active acid which forms salts with the racemic compound and separation of the salts obtained in this manner, for example by virtue of their different solubilities, and the antipodes can be liberated from the diastereomers by the action of suitable agents. Particularly customary optically active acids are, for example, the D- and L-forms of tartaric acid, di-o-toluyltartaric acid, malic acid, mandelic acid, camphorsulphonic acid or quinic acid.

The invention also relates to those embodiments of the process in which a compound obtained at any stage of the process as an intermediate product is used as a starting material and the missing process stages are carried out, or the process is discontinued at any stage, or a starting material is formed under the reaction conditions, or a reaction component is present in a given case in the form of its salt.

For carrying out the reactions according to the invention it is advisable to use those starting substances which yield the groups of end products which have been especially mentioned initially and particularly the end products which have been especially described or singled out.

The starting substances are known or, if they are new, can be manufactured by methods which are in themselves known.

The new compounds can be used, for example, in the form of pharmaceutical preparations in which they are present in the free form or, if appropriate, in the form of their salts, especially the therapeutically usable alkali metal salts, mixed with a pharmaceutical organic or inorganic, solid or liquid excipient which is suitable, for example, for enteral, parenteral, or topical application. Possible substances for making up the latter are those which do not react with the new compounds, such as, for example, water, gelatine, lactose, starch, stearyl alcohol, magnesium stearate, talc, vegetable oils, benzyl alcohols, gum, propylene glycols, white petroleum jelly or other known medicinal excipients. The pharmaceutical preparations can be, for example, in the form of tablets, dragees, capsules, suppositories, creams or ointments or in liquid form as solutions (for example as an elixir or syrup), suspensions or emulsions. If appropriate, they are sterilised and/or contain auxiliary substances, such as preservatives, stabilisers, wetting or emulsifying agents, solubilisers or salts for modifying the osmotic pressure or buffers. They can also contain other therapeutically valuable substances. The pharmaceutical preparations are obtained according to customary methods. The recommended daily dose for a warm-blooded animal weighing about 75 kg is about 100–300 mg.

The invention is described in more detail in the examples which follow.

EXAMPLE 1

40 g of 2-bromopyridine in 50 ml of absolute ether are added dropwise slowly at −60° C with stirring and in a nitrogen atmosphere to 175 ml of a 1.5 N solution of butyl-lithium in ether, followed, 15 minutes after the completion of the addition, by a solution of 15 g of p-(1-cyclohexenyl)-benzoic acid in 250 ml of absolute ether. The cooling bath is then removed, the reaction mixture is allowed to warm up to room temperature and it is stirred for 2 hours at room temperature. Working up is carried out by pouring the reacton solution onto a mixture of ice and ammonium chloride and partitioning it between ether and water. The ether phase is separated off and washed successively with water, 0.1 N sodium hydroxide solution and water, dried over sodium sulphate and evaporated under reduced pessure. Distillation under reduced pressure of the evaporation residue yields, in the fraction boiling at 200° C (0.9 mm Hg), crude 2-{[p-(1-cyclohexenyl)-phenyl]-oxomethyl}-pyridine of the formula

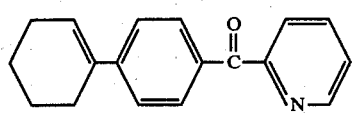

of melting point 58°-60° C.

EXAMPLE 2

2-[3-Chloro-4-cyclohexyl-phenyl)-oxomethyl]-pyridine of the formula

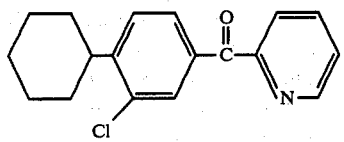

of melting point 67°-69° C, is obtained in a manner analogous to that described in Example 1 by reacting 2-bromopyridine and butyl-lithium with 3-chloro-4-cyclohexylbenzoic acid.

The 3-chloro-4-cyclohexylbenzoic acid used as starting material can be prepared as follows.

To a solution of 60 g of sodium hydroxide in 2,400 ml of water are added dropwise with stirring, at 0° C, 720 g of bromine followed, at 30°-40° C, by 200 g of 3-chloro-4-cyclohexylacetophenone in 1,000 ml of dioxane. Stirring is continued overnight at room temperature and the mixture is then cooled to 0° C and 400 g of sodium bisulphite are added in portions with stirring. The mixture is allowed to stand for 2 hours at room temperature, the dioxane is evaporated off under reduced pressure, 1,500 ml of water are added and the pH is adjusted to 1 with concentrated hydrochloric acid. The precipitate formed is then filtered off, washed thoroughly with water and recrystallised from ethyl acetate.

The 3-chloro-4-cyclohexylbenzoic acid thus obtained melts at 177°-179° C.

EXAMPLE 3

33.5 g of 2-bromopyridine in 100 ml of absolute ether are added dropwise with stirring and in a nitrogen atmosphere at −60° C, over the course of 30 minutes, to 150 ml of a 1.5 N solution of butyl-lithium in ether, and subsequently 17.3 g of α-[p-(1-cyclohexenyl)-phenyl]-propionic acid in 100 ml of absolute ether are added similarly over the course of one hour. Stirring is continued for one hour at −60° C, the temperature is then allowed to rise to −5° C and 100 ml of water are added slowly, whereupon the brown precipitate formed goes into solution again. The water phase is separated off and the ether phase is washed successively with 2 lots of 100 ml of water, 100 ml of saturated aqueous ammonium chloride solution, twice 100 ml of 2 N sodium hydroxide solution and 100 ml of water, dried over sodium sulphate and evaporated under reduced pressure. 2-{2-[p-(1-Cyclohexenyl)-phenyl]-1-oxo-propyl}-pyridine of the formula

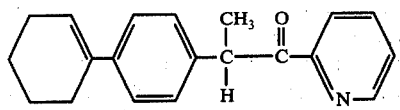

of melting point 81°-83° C crystallises from the evaporation residue after the addition of cold ethanol.

EXAMPLE 4

Starting from α-[p-(1-cyclohexenyl)-phenyl]-propionic acid and 2-bromo-5-methylpyridine, 2-{2-[p-(1-cyclohexenyl)-phenyl]-1-oxo-propyl}-6-methylpyridine of the formula

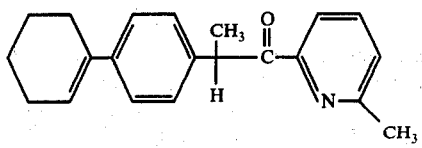

of melting point 69.5°-71.5° C (from cold ethanol), is obtained in a manner analogous to that described in Example 3.

EXAMPLE 5

4-{2-[p-(1-Cyclohexenyl)-phenyl]-1-oxo-propyl}-pyridine of the formula

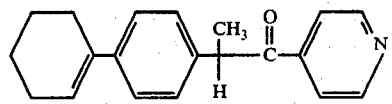

of melting point 88°-90° C (from a little cold ethanol), is obtained in a manner analogous to that described in Example 3, starting from α-[p-(1-cyclohexenyl)-phenyl]-propionic acid and 4-bromopyridine.

EXAMPLE 6

2-[2-(3-Chloro-4-cyclohexyl-phenyl)-1-oxo-propyl]-pyridine of the formula

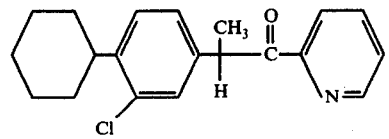

of boiling point 160°-170° C/0.01 mm Hg, is obtained in a manner analogous to that described in Example 3, starting from α-[3-chloro-4-cyclohexyl-phenyl]-propionic acid.

EXAMPLE 7

2-[2-(p-Cyclohexylphenyl)-1-oxo-propyl]-pyridine of the formula

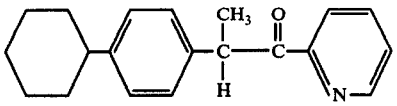

of melting point 80°-81° C (from ethanol), is obtained in a manner analogous to that described in Example 3, starting from α-(p-cyclohexylphenyl)-propionic acid.

EXAMPLE 8

2-[(p-Cyclohexylphenyl)-oxo-methyl]-pyridine of the formula

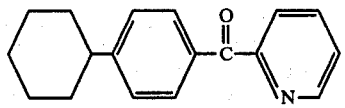

of melting point 44°-45° C (from ethanol) and boiling point 185°-190° C/0.35 mm Hg, is obtained in a manner analogous to that described in Example 1 by reacting a 2-bromopyridine and butyl-lithium with p-cyclohexylbenzoic acid.

EXAMPLE 9

To a stirred solution of 40 g of phenylcyclohexane in 300 ml of ethylene chloride are added, at 0° C and in an anhydrous atmosphere, 89.5 g of nicotinic acid chloride hydrochloride, and subsequently 100 g of finely powdered aluminium chloride are added in portions over the course of 30 minutes. The mixture is stirred for a further 90 minutes at 10° C and is stirred overnight at room temperature and then poured onto 1 kg of ice, the pH is adjusted to 2 with concentrated hydrochloric acid and the mixture is extracted with 3 times 800 ml of ether. The organic phases are combined and are washed with 800 ml of saturated sodium bicarbonate solution and with the same quantity of water and are dried over sodium sulphate, treated with active charcoal and evaporated in vacuo. Vacuum distillation of the evaporation residue yields a main fraction boiling at 120°–200° C/0.05 mm Hg.

The distillate thus obtained is chromatographed on 400 g of silica gel using chloroform as eluant. A non-polar impurity is obtained first. Subsequent elution with ether and fractional crystallisation from cold hexane yields 3-[(p-cyclohexylphenyl)-oxo-methyl]-pyridine of the formula

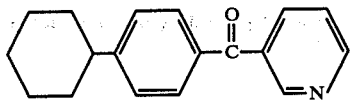

of melting point 52°–54° C (hydrochloride: 157°–158° C).

EXAMPLE 10

A solution of 3.0 g of crude α-(2-pyridoyl)-α-[p-(1-cyclohexenyl)-phenyl]-propionic acid (sic) in 30 ml of pyridine is heated under reflux for 3 hours. The mixture is then evaporated to dryness in vacuo and the evaporation residue is chromatographed on 100 g of silica gel using chloroform as eluant. Fractions are collected every 50 ml. Fractions 6-8 contain crude 2-{2[p-(1-cyclohexenyl)-phenyl]-1-oxo-propyl}-pyridine of the formula

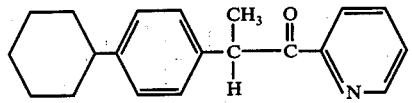

of melting point 81°–83° C (after fractional crystallisation from cold ethanol).

The α-(2-pyridoyl)-α-[p-(1-cyclohexenyl)-phenyl]-propionic acid used as starting material can be prepared as follows:

15.3 ml of butyl-lithium (2.6 N solution in hexane) are added dropwise with stirring, in a dry nitrogen atmosphere at −5° C, to a solution of 4.0 g of diisopropylamine in 28 ml of absolute tetrahydrofurane, and subsequently a solution of 7.3 g of α-[p-(1-cyclohexenyl)-phenyl]-propionic acid methyl ester in 20 ml of absolute tetrahydrofurane is added similarly at −15° C over the course of 30 minutes. The mixture is stirred for a further 20 minutes at −20° C, cooled to −78° C and 7.1 g of picolinic acid chloride are added all at once and the mixture is stirred for a further hour at −5° C. The reaction mixture is then poured onto 100 g of ice and extracted with 3 times 100 ml of methylene chloride. The organic phases are combined, washed successively with 100 ml of saturated aqueous sodium bicarbonate solution, with 100 ml of 2 N aqueous acetic acid and with 3 times 100 ml of water, dried over sodium sulphate and evaporated in vacuo. The evaporation residue is dissolved in 100 ml of ethanol, 100 ml of 2 N sodium hydroxide solution are added and the reaction mixture is stirred overnight at room temperature. It is then neutralised with 2 N hydrochloric acid and evaporated to dryness in vacuo. The crude, oily α-(2-pyridoyl)-α-[p-(1-cyclohexenyl)-phenyl]-propionic acid which remains in the evaporation residue is processed further without additional purification.

EXAMPLE 11

10.0 g of chromium trioxide are added in portions at 5° C, whilst stirring and with exclusion of moisture, to a solution of 15.8 ml of pyridine in 200 ml of absolute methylene chloride, behind a protective shield. After the completion of the addition the mixture is stirred for a further 30 minutes at room temperature, 2.8 g of crude 2-[(p-cyclohexylphenyl)-hydroxymethyl]-pyridine, dissolved in 10 ml of methylene chloride, are then added all at once and the mixture is stirred for a further 20 minutes at room temperature. The mixture is decanted off from the brown resin which is formed and is partitioned at 0° C between 50 ml of methylene chloride and 2 lots of 50 ml of saturated sodium bicarbonate solution. The organic phase is washed successively with twice 50 ml of 0.1 N hydrochloric acid and twice 50 ml of water, dried over sodium sulphate and evaporated in vacuo. Chromatography of the evaporation residue on 200 g of silica gel, using chloroform as eluant, and fractional crystallisation from cold ethanol, yields 2-[(p-cyclohexylphenyl)-oxomethyl]-pyridine of the formula

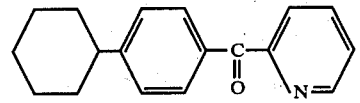

of melting point 44°–45° C (boiling point 185°–190°/0.35 mm).

The 2-[(p-cyclohexylphenyl)-hydroxymethyl]-pyridine used as starting material can be prepared in the following way:

24.8 g of p-cyclohexylbromobenzene, dissolved in 50 ml of absolute tetrahydrofurane, are added slowly dropwise, in an anhydrous atmosphere and with stirring, to 2.5 g of magnesium shavings covered with a little absolute tetrahydrofurane, in such a manner that the temperature does not exceed 50° C. After the completion of the addition, the reaction solution is stirred for a further 30 minutes at 50° C, allowed to cool to room temperature and added dropwise, under anhydrous conditionings and with stirring, to a solution of 10 g of pyridine-2-aldehyde in 50 ml of absolute tetrahydrofurane, at such a rate that the temperature of the reaction mixture is between 0° and 5° C. After the completion of the addition, the reaction solution is stirred overnight at room temperature and poured into a mixture of 500 g of ice and 100 ml of 1 N hydrochloric acid and the mixture is extracted with 3 times 200 ml of methylene chloride. The organic phases are washed with 3 lots of 200 ml of water, dried over sodium sulphate and evaporated in vacuo. The crude 2-[(p-cyclohexylphenyl)-hydroxymethyl]-pyridine, IR spectrum: $v_{c=o}$ = 3,600 cm$^{-1}$ (in methylene chloride), which is contained in the evaporation residue is processed further without additional purification.

EXAMPLE 12

A solution of 5 g of 2-{2-[p-(1-cyclohexenyl)-phenyl]-1-oxo-propyl}-pyridine in 100 ml of ethanol is heated to the boil with 4 g of hydroxylamine hydrochloride and 4 g of anhydrous sodium sulphate. 35 ml of water are added to the hot solution and the now homogeneous solution is heated under reflux for 10 minutes, evaporated to a third of its volume and allowed to cool to room temperature. The evaporation residue is partitioned twice between 50 ml of methylene chloride and 50 ml of water. The combined organic phases are dried over sodium sulphate and evaporated in vacuo.

The two stereoisomeric 2-{2-[p-(1-cyclohexenyl)-phenyl]-1-hydroxyimino-propyl}-pyridines of the formula

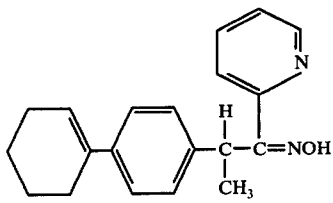

of melting point 170°–173° C and melting point 150° C respectively, are obtained from the evaporation residue by fractional crystallisation from benzene-pentane.

EXAMPLE 13

Tablets containing 100 mg of 2-{2-[p-(1-cyclohexenyl)-phenyl]-1-oxo-propyl}-pyridine can be manufactured, for example, with the following composition:

| Composition | per tablet |
| --- | --- |
| Active substance | 100.0 mg |
| Wheat starch | 90.0 mg |
| Lactose | 120.0 mg |
| Colloidal silicic acid | 10.0 mg |
| Talc | 18.0 mg |
| Magnesium stearate | 2.0 mg |
| | 340.0 mg |

MANUFACTURE

The active substance is mixed with a portion of wheat starch and with the lactose and the colloidal silicic acid and the mixture is forced through a sieve. A further portion of wheat starch is made into a paste with a 5-fold quantity of water on the water bath and the powdery mixture is kneaded with this paste until a slightly plastic composition is formed.

The plastic composition is pressed through a sieve of approx. 3 mm mesh width and is dried and the dried granules are forced through a sieve. The remaining wheat starch, the talc and the magnesium stearate are then mixed in. The resulting mixture is pressed into tablets of 280 mg with breaking grooves.

We claim:
1. Pyridine compounds of the general formula I

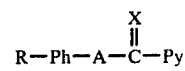

wherein R denotes a cycloalkenyl or cycloalkyl radical with 5 to 10 ring members which is unsubstituted or substituted by $C_1$–$C_4$-alkyl, $C_2$–$C_4$-alkenyl, $C_1$–$C_4$-alkoxy, hydroxy or oxo, 2- or 3-bicyclo[4,4,0]-decyl or -dec-2-enyl, 2-bicyclo[2,2,2]-octyl or -oct-2-enyl, 2-bornyl, 2-norbornyl, 2-bornenyl, 2-norbornenyl, 1-homoadamantyl, octahydro-1,2,4-methenopentalenyl which is unsubstituted or substituted by $C_1$–$C_4$-allyl or $C_1$–$C_4$-alkoxy, or 1- or 2-adamantyl, Ph denotes p-phenylene optionally substituted by nitro, trifluoromethyl, $C_1$–$C_4$-alkyl, $C_1$–$C_4$-alkoxy, chlorine, fluorine or bromine, A denotes a direct bond, X denotes an oxo group, and Py denotes a pyridyl radical which is unsubstituted or C-substituted by $C_1$–$C_4$-alkyl or $C_1$–$C_4$-alkoxy, or a therapeutically acceptable acid addition salt thereof.

2. A compound as claimed in claim 1 of the formula I wherein R denotes a cyclopentyl, cyclohexyl, cycloheptyl, cyclooctyl, 1-cyclopentenyl, 1-cyclohexenyl, 1-cycloheptenyl or 1-cyclooctenyl radical which is unsubstituted or substituted by $C_1$–$C_4$-alkyl or $C_1$–$C_4$-alkoxy, or unsubstituted 1- or 2-adamantyl, Ph denotes p-phenylene which is unsubstituted or substituted by nitro, trifluoromethyl, $C_1$–$C_4$-alkyl, $C_1$–$C_4$-alkoxy, chlorine, fluorine or bromine, A denotes a direct bond, X denotes an oxo group and Py denotes a pyridyl radical which is unsubstituted or C-substituted by $C_1$–$C_4$-alkyl or $C_1$–$C_4$-alkoxy, or a therapeutically acceptable acid addition salt therof.

3. A compound as claimed in claim 1 of the formula I wherein R denotes a cyclopentyl, cyclohexyl, cycloheptyl, cyclooctyl, 1-cyclopentenyl, 1-cyclohexenyl, 1-cycloheptenyl or 1-cyclooctenyl which is unsubstituted or substituted by methyl or methoxy, or unsubstituted 1- or 2-adamantyl, Ph denotes p-phenylene which is unsubstituted or substituted by methyl, methoxy or chlorine, A denotes a direct bond, X denotes the oxo group and Py denotes a pyridyl radical which is unsubstituted or C-substituted by methyl or methoxy, or a therapeutically acceptable acid addition salt thereof.

4. A compound as claimed in claim 1 of the formula I wherein R denotes cyclopentyl, 1-cyclopentenyl, cyclooctyl, 1-cyclooctenyl, cyclohexyl, 1-cyclohexenyl, cycloheptyl, 1-cycloheptenyl or 2- or 1-adamantyl, Ph denotes p-phenylene which is unsubstituted or substituted in the o-position to R by methyl, methoxy or chlorine, X denotes oxo group, A denotes a direct bond and Py denotes a pyridyl radical which is unsubstituted or C-methylated, or a therapeutically acceptable acid addition salt thereof.

5. A compound as claimed in claim 4 being 2-[(3-chloro-4-cyclohexyl-phenyl)-oxomethyl]-pyridine or a therapeutically acceptable acid addition salt thereof.

6. A compound as claimed in claim 4 being 2-[(p-cyclohexylphenyl)-oxomethyl]-pyridine or a therapeutically acceptable acid addition salt thereof.

7. 3-[(p-cyclohexylphenyl)-oxomethyl]-pyridine or a therapeutically acceptable acid addition salt thereof.

8. 2-{[p-(1-cyclohexenyl)-phenyl]-oxomethyl}-pyridine or a therapeutically acceptable acid addition salt thereof.

9. An antiinflammatory pharmaceutical preparation comprising an antiinflammatory effective amount of a compound claimed in claim 1 together with a conventional pharmaceutical excipient.

* * * * *